(12) United States Patent
Ionescu et al.

(10) Patent No.: US 8,058,424 B2
(45) Date of Patent: *Nov. 15, 2011

(54) SYNTHESIS OF 5-AZACYTIDINE

(75) Inventors: Dumitru Ionescu, Ann Arbor, MI (US);
Peter Blumbergs, Royal Oak, MI (US)

(73) Assignee: Pharmion LLC, Summit, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/973,701

(22) Filed: Dec. 20, 2010

(65) Prior Publication Data
US 2011/0092694 A1  Apr. 21, 2011

Related U.S. Application Data

(63) Continuation of application No. 12/208,238, filed on Sep. 10, 2008, now Pat. No. 7,858,774, which is a continuation of application No. 11/381,275, filed on May 2, 2006, now abandoned, which is a continuation of application No. 10/390,526, filed on Mar. 17, 2003, now Pat. No. 7,038,038.

(51) Int. Cl.
| C07H 19/00 | (2006.01) |
| C07H 19/048 | (2006.01) |
| C07H 5/04 | (2006.01) |
| C07H 5/06 | (2006.01) |
| C08B 37/00 | (2006.01) |
| A01N 43/04 | (2006.01) |
| A61K 31/70 | (2006.01) |

(52) U.S. Cl. .................. 536/55.3; 536/28.2; 514/43
(58) Field of Classification Search .................. None
See application file for complete search history.

(56) References Cited

U.S. PATENT DOCUMENTS

| 3,350,388 | A | 10/1967 | Sorm et al. |
| 3,817,980 | A | 6/1974 | Vorbruggen et al. |
| 3,891,623 | A | 6/1975 | Vorbruggen et al. |
| 4,082,911 | A | 4/1978 | Vorbruggen |
| 4,209,613 | A | 6/1980 | Vorbruggen |
| 6,642,206 | B2 | 11/2003 | Ramasamy et al. |
| 6,887,855 | B2 | 5/2005 | Ionescu et al. |
| 6,943,249 | B2 | 9/2005 | Ionescu et al. |
| 7,038,038 | B2 | 5/2006 | Ionescu et al. |
| 7,078,518 | B2 | 7/2006 | Ionescu et al. |
| 7,700,770 | B2 | 4/2010 | Ionescu et al. |
| 7,772,199 | B2 | 8/2010 | Ionescu et al. |
| 7,858,774 | B2 | 12/2010 | Ionescu et al. |
| 2010/0292180 | A1 | 11/2010 | Ionescu et al. |
| 2010/0298253 | A1 | 11/2010 | Ionescu et al. |

FOREIGN PATENT DOCUMENTS

| CZ | 114716 | 11/1964 |
| CZ | 116297 | 4/1965 |
| DE | 1922702 | 11/1969 |
| DE | 2012888 | 9/1971 |
| FR | 2123632 | 9/1972 |
| GB | 1227691 | 4/1971 |
| GB | 1227692 | 4/1971 |

OTHER PUBLICATIONS

Beisler et al., *J. Carbohydrates Nucleosides Nucleotides*, 4(5): 281-99 (1977).
Beisler, *J. Med. Chem.*, 21(2): 204-08 (1978).
Chan, K.K. et al., *J. Pharm. Sci.*, 68(7): 807-12 (1979).
Gaubert et al., *Nucleosides, Nucleotides & Nucleic Acids*, 20(4-7): 837-40 (2001).
Kornblith et al., *J. Clin Oncol.*, 20(10): 2441-52 (2002).
Niedballa et al., *J. Org. Chem.*, 39(25): 3672-74 (1974).
Piskala et al., *Collect. Czech. Chem. Commun.*, 29: 2060-76 (1964).
Piskala et al., *Nucleic Acid Chem.*, 1: 435-41 (1978).
Piskala et al., *Nucleic Acids Research*, Special Pub. No. 1: s17-20 (1975).
Silverman et al., *J. Clin. Oncol.*, 20(10): 2429-40 (2002).
Vorbruggen et al., *Chem. Ber.*, 114: 1279-86 (1981).
Vorbruggen et al. in Organic Reactions, vol. 55, 100 (L.A. Paquette ed., John Wiley & Sons, New York, 2000).
Vorbruggen et al., *Chem. Ber.*, 114: 1234-55 (1981).
Winkley et al., *J. Org. Chem.*, 35(2): 491-95 (1970).
Wittenburg et al., *Zeitschrift fur Chemie*, 4: 303-04 (1964).
Zaitseva et al., *Bioorg. & Med. Chem. Lett.*, 5(24): 2999-3002 (1995).
International Search Report for WO2004/82618, dated Sep. 21, 2004.
Office Action in U.S. Appl. No. 10/390,526, mailed Dec. 3, 2003.
Office Action in U.S. Appl. No. 10/390,526, mailed Oct. 21, 2004.
Office Action in U.S. Appl. No. 10/390,526, mailed Apr. 6, 2005.
Notice of Allowability in U.S. Appl. No. 10/390,526, mailed Dec. 1, 2005.
Office Action in U.S. Appl. No. 11/381,275, mailed Mar. 8, 2007.
Office Action in U.S. Appl. No. 11/381,275, mailed Dec. 18, 2007.
Office Action in U.S. Appl. No. 10/390,578, mailed Jul. 1, 2004.
Notice of Allowability in U.S. Appl. No. 10/390,578, mailed Dec. 29, 2004.
Notice of Allowability in U.S. Appl. No. 11/052,615, mailed Mar. 9, 2006.
Office Action in U.S. Appl. No. 11/458,365, mailed Mar. 12, 2007.
Office Action in U.S. Appl. No. 11/458,365, mailed Feb. 27, 2008.
Office Action in U.S. Appl. No. 11/458,365, mailed Nov. 28, 2008.
Office Action in U.S. Appl. No. 11/458,365, mailed Aug. 4, 2009.

(Continued)

*Primary Examiner* — Layla Bland

(57) ABSTRACT

The present invention provides a method for the preparation of 5-azacytidine, wherein 5-azacytidine is represented by the structure:

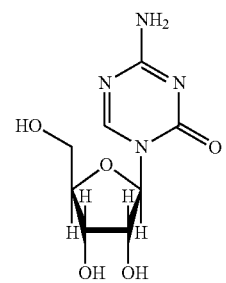

The method involves the silylation of 5-azacytosine, followed by the coupling of silylated 5-azacytosine to a protected β-D-ribofuranose derivative. The coupling reaction is catalyzed by trimethylsilyl trifluoromethanesulfonate (TMS-Triflate).

31 Claims, No Drawings

OTHER PUBLICATIONS

Notice of Allowability in U.S. Appl. No. 11/458,365, mailed Jan. 26, 2010.
Notice of Allowability in U.S. Appl. No. 10/390,530, mailed May 13, 2005.
Office Action in U.S. Appl. No. 11/198,550, mailed Aug. 1, 2007.
Office Action in U.S. Appl. No. 11/198,550, mailed May 12, 2008.
Office Action in U.S. Appl. No. 11/198,550, mailed Oct. 2, 2008.
Notice of Allowability in U.S. Appl. No. 11/198,550, mailed Feb. 24, 2009.
Notice of Allowability in U.S. Appl. No. 11/198,550, mailed Jul. 31, 2009.
Notice of Allowability in U.S. Appl. No. 11/198,550, mailed Dec. 2, 2009.
Ault, *Techniques and Experiments for Organic Chemistry*, 6$^{th}$ ed., University Science Books, 59-60 (1998).
Office Action in U.S. Appl. No. 12/208,238, mailed Nov. 13, 2009.
Office Action in U.S. Appl. No. 12/208,238, mailed May 12, 2010.
Notice of Allowability in U.S. Appl. No. 12/208,238, mailed Aug. 26, 2010.

SYNTHESIS OF 5-AZACYTIDINE

RELATED APPLICATIONS

This application is a continuation of U.S. patent application Ser. No. 12/208,238, filed Sep. 10, 2008, entitled "Synthesis of 5-Azacytidine," now U.S. Pat. No. 7,858,774, which is a continuation of U.S. patent application Ser. No. 11/381,275, filed May 2, 2006, entitled "Synthesis of 5-Azacytidine," now abandoned, which is a continuation of U.S. patent application Ser. No. 10/390,526, filed Mar. 17, 2003, entitled "Synthesis of 5-Azacytidine," now U.S. Pat. No. 7,038,038, issued on May 2, 2006, the contents of each of which are hereby incorporated by reference herein in their entireties.

FIELD OF THE INVENTION

The invention relates to the synthesis of 5-azacytidine (also known as azacitidine and 4-amino-1-β-D-ribofuranosyl-5-triazin-2(1H)-one). 5-azacytidine may be used in the treatment of disease, including the treatment of myelodysplastic syndromes (MDS).

BACKGROUND OF THE INVENTION 5-azacytidine (also known as azacitidine and 4-amino-1-β-D-ribofuranosyl-S-triazin-2(1H)-one; Nation Service Center designation NSC-102816; CAS Registry Number 320-67-2) has undergone NCI-sponsored trials for the treatment of myelodysplastic syndromes (MDS). See Kornblith et al., J. Clin. Oncol. 20(10): 2441-2452 (2002) and Silverman et al., J. Clin. Oncol. 20(10): 2429-2440 (2002). 5-azacytidine may be defined as having a formula of $C_8H_{12}N_4O_5$, a molecular weight of 244.20 and a structure of

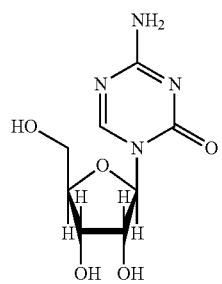

The s-triazine ring of 5-azacytidine has a particular sensitivity to water (see J. A. Beisler, J. Med. Chem., 21, 204 (1978)); this characteristic has made the synthesis of 5-azacytidine a challenge, especially in manufacturing at commercial scale. A number of prior art methods have been developed in order to avoid the use of water; however, these methods all have additional problems that render them undesirable for the production of large-scale batches of 5-azacytidine. For example, Piskala and Sorm teach the following synthesis scheme in (see U.S. Pat. No. 3,350,388; A. Piskala and F. Sorm, Collect. Czech. Chem. Commun., 29, 2060 (1964); and A. Piskala and F. Sorm, Ger. 1922702 (1969), each of which is incorporated herein by reference in its entirety):

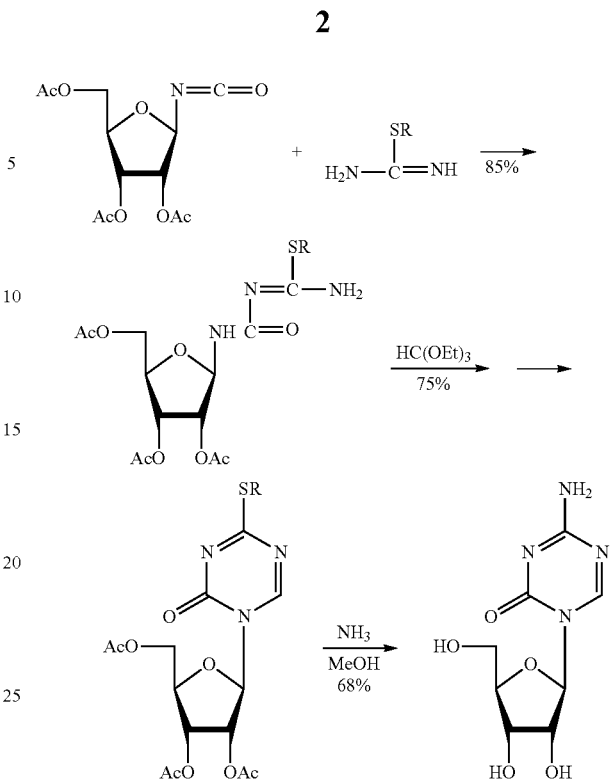

The overall yield of this scheme is 43.3%. This method involves a reactive starting material (isocyanate) with a controlled stereochemistry (1-β configuration). Such a compound cannot be regarded as a starting material. The drawbacks of this scheme include the presence of steps that are difficult to scale-up, the use of benzene as solvent in one step, and the requirement for a deprotection step performed in a closing pressure vessel using dry ammonia. Furthermore, the final 5-azacytidine product was isolated from the reaction mixture by filtration with no further purification; this is not acceptable for the synthesis of an Active Pharmaceutical Ingredient (API) for human use. The addition of further purification steps will further reduce the overall yield.

Winkley and Robins teach an 5-azacytidine synthesis process that relies on the coupling of a "bromosugar" with a silyl derivative of 5-azacytosine (see M. W. Winkley and R. K. Robins, J. Org. Chem., 35, 491 (1970), incorporated by reference in its entirety):

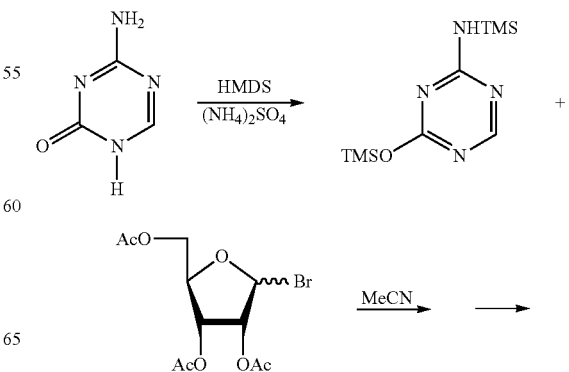

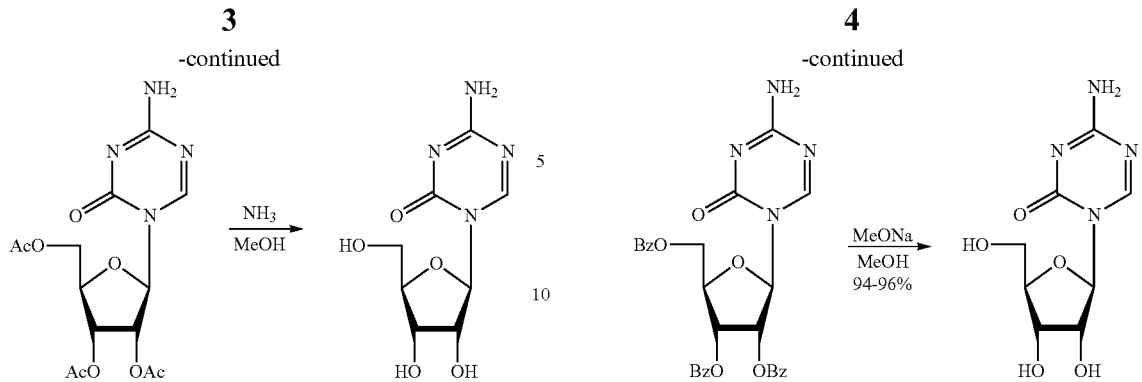

In this procedure, 5-azacytosine was treated with excess hexamethyldisilazane (HMDS) in the presence of catalytic amounts of ammonium sulfate at reflux until a complete solution was generated (TMS=(CH$_3$)$_3$Si). See E. Wittenburg, Z. Chem., 4, 303 (1964) for the general procedure. The excess HMDS was removed by vacuum distillation and the residue was used directly (without further purification) in the coupling with, 2,3,5-tri-O-acetyl-D-ribofuranosyl bromide in acetonitrile. The coupled product was deprotected with methanolic ammonia solution.

There are many significant weaknesses in this procedure. First, the fact that the bromosugar was a mixture of anomers, which means that the final coupled product was also a mixture of anomers. Second, the work-up in the coupling step involved a great many steps, specifically: concentration of the reaction mixture to dryness; treatment of the residue with sodium bicarbonate, water and methanol; removal of the water by co-evaporation with absolute ethanol; extraction of the residue with chloroform twice; and finally the concentration to dryness of the combined chloroform in extract. Third, ammonia in MeOH was used in the deprotection step, which requires the use of a pressure vessel. Fourth, the crude 5-azacytidine was isolated in only a 35% yield. This crude material was then dissolved in warm water and the solution was decolorized with charcoal. Evaporation then gave crystals of 5-azacytidine with a yield 11%. This material was further recrystallized from aqueous ethanol (charcoal). The low recovery during purification can be correlated with the poor anomeric ratio and with the known low stability of 5-azacytidine in water.

Piskala and Sorm also teach the following process for coupling involving the use of a "chlorosugar" (A. Piskala and F. Sorm, Nuci. Acid Chem. 1, 435 (1978), incorporated herein by reference in its entirety):

2,3,5-Tri-O-Benzoyl-D-ribofuranosyl chloride was prepared by saturating a solution of 1-O-acetyl-2,3,5-tri-O-benzoyl-β-D-ribose in ClCH$_2$CH$_2$Cl—AcCl with gaseous HCl (with ice-cooling) and then keeping the mixture overnight at room temperature. This procedure is difficult to scale-up with plant equipment due to the special handling requirements of gaseous HCl. Also, the typical α/β ratio in the chlorosugar is unknown, as is the impact of the α/β ratio on the yield and final purity of 5-azacytidine.

Piskala, Fiedler and Sorm teach a procedure for the ribosylation of silver salts of 5-azapyrimidine nucleobases in A. Piskala, P. Fiedler and F. Sorm, Nucleic Acid Res., Spec. Publ. 1, 17 (1975), incorporated herein by reference in its entirety. Specifically, they teach that the ribosylation of the silver salt of 5-azacytosine with 2,4,5-tri-O-benzoyl-D-ribosyl chloride gives 5-azacytidine. This is clearly not a procedure that is amenable to scale up for the large-scale production of 5-azacytidine.

Niedballa and Vorbrüggen teach the procedure that has been used historically for the large-scale synthesis of 5-azacytidine for the above-mentioned NCI-sponsored trials for the treatment of myelodysplastic syndromes. See H. Vorbrüggen and U. Niedballa, Ger. 2,012,888 (1971) and U. Niedballa and H. Vorbrüggen, J. Org. Chem., 39, 3672 (1974), each of which is incorporated herein by reference in its entirety. The procedure involves the following steps:

There are at least three major drawbacks to this procedure. First, and most importantly,

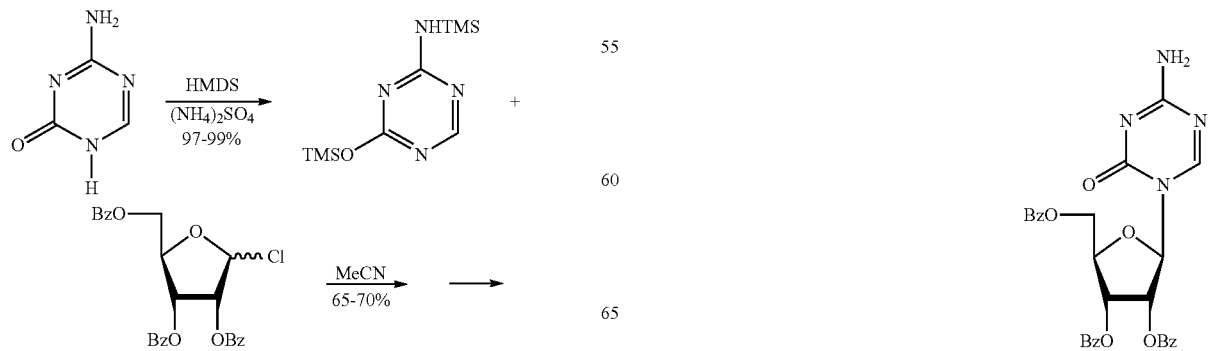

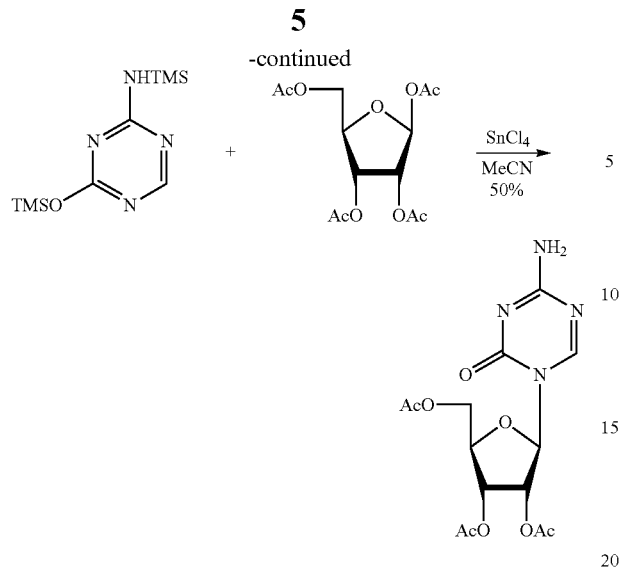

after purification, variable amounts of tin from one batch to another were found in the API. The lack of control of the tin level means that the procedure is not suitable for producing an API for human use. Second, emulsions developed during the workup of the coupling mixture. Indeed, H. Vorbrüggen and C. Ruh-Pohlenz in *Organic Reactions*, Vol. 55, 2000 (L. A. Paquette Ed., John Wiley & Sons, New York), p 100, have previously noted that silylated heterocycles and protected 1-O-acyl or 1-O-alkyl sugars in the presence of Friedel-Crafts catalysts like $SnCl_4$ often form emulsions and colloids during work-up. The phase separation of the emulsion is slow, so the water-sensitive protected 5-azacytidine was exposed to water for variable periods of time leading to variable amounts of decomposition. Third, a filtration step was performed in order to isolate the insoluble tin salt. Typically, this filtration is very slow, and is likely the reason that variations in the final yield were noted. These problems mean that the process is not conveniently amenable to scale-up.

Vorbrüggen et al. in *Chemische Berichte*, 114: 1234-1255 (1981) teach the use of certain Lewis acids as Friedel-Crafts catalysts for the coupling of silylated bases with 1-O-acyl sugars. In particular, they teach the coupling of silylated bases with 1-O-acyl sugars in the presence of trimethylsilyl trifluoromethanesulfonate (TMS-Triflate) in 1,2-dichloroethane or acetonitrile. The reaction mixture was then diluted with dichloromethane and the organic phase extracted with ice-cold saturated $NaHCO_3$. The use of this procedure to synthesize 5-azacytidine is not taught or suggested.

Vorbrüggen and Bennua in *Chemische Berichte*, 114: 1279-1286 (1981) also teach a simplified version of this nucleoside synthesis method in which base silylation, generation of the Lewis acid Friedel-Crafts catalyst, and coupling of the silylated base to the 1-O-acyl sugar takes place in a one step/one pot procedure employing a polar solvent such as acetonitrile. Following reaction, dichloromethane is added, and the mixture is extracted with aqueous $NaHCO_3$. The use of this procedure to synthesize 5-azacytidine is not taught or suggested. Moreover, this one step/one pot reaction is not suitable for the synthesis of 5-azacytidine because the extraction is done is the presence of acetonitrile. Acetonitrile is a polar solvent, and is therefore miscible with water. As a consequence, the protected 5-azacytidine in the acetonitrile is exposed during extraction to the aqueous phase for variable amounts of time, which in turn leads to variable amounts of decomposition of the protected 5-azacytidine.

Thus, there is an unmet need in the field for the provision of a simple, controlled procedure for the synthesis of 5-azacytidine that provides an API that is suitable for use in humans, minimizes the exposure of 5-azacytidine to water, and is amenable to scaling-up for the production of large quantities of 5-azacytidine.

SUMMARY OF THE INVENTION

The present invention provides for the first time a method that synthesizes 5-azacytidine that is suitable for use in humans and is amenable to large scale synthesis.

In one series of embodiments, 5-azacytidine is prepared by:

a) reacting 5-azacytosine with a silylating reagent to yield a compound of the structure:

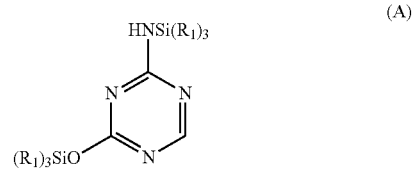

(A)

wherein each $R_1$ is an optionally substituted $C_1$-$C_{20}$ alkyl group independently selected from the group consisting of straight chain alkyl groups, branched alkyl groups, and cyclic alkyl groups;

b) coupling (A) with a compound of the structure:

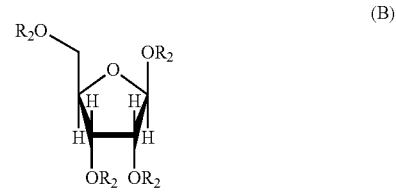

(B)

wherein each $R_2$ is an optionally substituted $C_1$-$C_{20}$ acyl group independently selected from the group consisting of straight chain acyl groups, branched acyl groups, and benzoyl groups, wherein the coupling of (A) and (B) is carried out in the presence of trimethylsilyl trifluoromethanesulfonate (TMS-Triflate), and wherein the coupling yields a compound of the structure

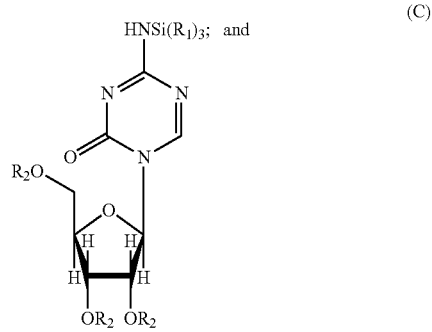

(C)

c) removing said $Si(R_i)_3$ and R2 groups from (C).

In preferred embodiments, the silylating reaction takes place in the absence of a solvent using an excess of silylating reagent, and optionally in the presence of a catalyst. If a catalyst is used, a preferred catalyst is ammonium sulfate. Preferably the silylating reagent is a trimethylsilyl (TMS) reagent (i.e., $R_1$=$CH_3$), or a mixture of two or more TMS reagents in excess over the 5-azacytosine. Preferred TMS reagents include hexamethyldisilizane (HINDS) and chlorotrimethylsilane (TMSC1). The silylated 5-azacytosine is preferably isolated prior to coupling by removing the silylating reagents using vacuum distillation, or by filtration.

Preferably, the compound (B) of coupling step b) is

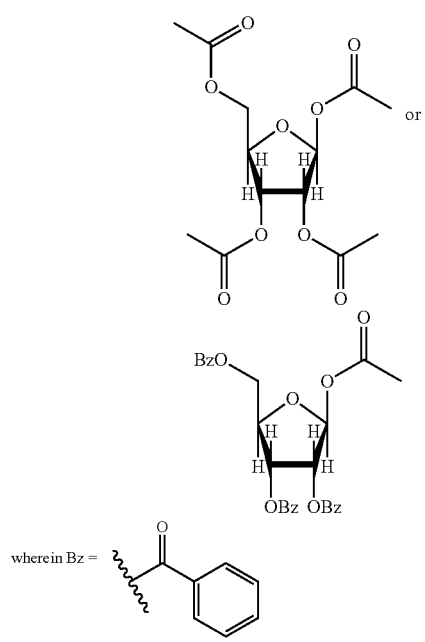

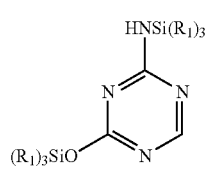

and the coupling reaction is carried out in a dry organic solvent, more preferably a dry organic non-polar solvent that is not miscible with water. Most preferably, the TMS-Triflate is quenched by extracting the reaction product of b) with, for example, an aqueous bicarbonate solution.

In another series of embodiments, a "one pot" synthesis of 5-azacytidine is provided comprising the steps of:

a) in a dry organic solvent, reacting 5-azacytosine with one or more silylating reagents to yield a compound having the structure;

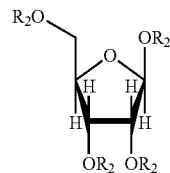

wherein each $R_1$ is an optionally substituted $C_1$-$C_{20}$ alkyl group independently selected from the group consisting of straight chain alkyl groups, branched alkyl groups, and cyclic alkyl groups;

b) adding directly to the reaction mixture of a) TMS-Triflate and a compound having the structure

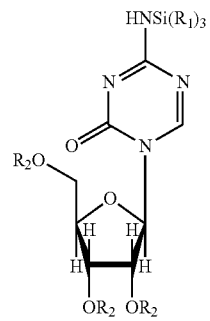

wherein each $R_2$ is an optionally substituted $C_1$-$C_{20}$ acyl group independently selected from the group consisting of straight chain acyl groups, branched acyl groups, and benzoyl group to yield a compound having the structure;

(C)

[structure C shown]

c) extracting the reaction mixture of b) with an aqueous quenching solution; and d) removing said $Si(R_i)_3$ and $R_2$ groups.

Preferably, the dry organic solvent of step a) is a polar solvent, most preferably acetonitrile. Preferably the polar solvent is removed between steps b) and c) and the reaction products of b) are dissolved in a dry organic non-polar solvent, most preferably dichloromethane of 1,2-dichlorethane, prior to step c).

In some embodiments, the crude 5-azacytidine produced by the above-described processes is subjected to one or more recrystallization procedures. For example, the crude 5-azacytidine may be dissolved in dimethylsulfoxide (DMSO), and then recrystallized by the addition of methanol.

The methods provided by the instant invention are amenable to scale-up, and avoid the use of tin catalysts and other metal ions, thereby providing 5-azacytidine that is suitable for use as an API. The methods also avoid the formation of emulsions during the work up (quenching/extraction) of the coupling reaction, thereby avoiding hydrolysis of the s-triazine ring.

DETAILED DESCRIPTION OF THE PREFERRED EMBODIMENTS

In the most basic embodiment of the invention, 5-azacytidine is synthesized according to the following process wherein each $R_1$ is an optionally substituted $C_1$-$C_{20}$ alkyl group independently selected from the group consisting of straight chain alkyl groups, branched alkyl groups, and cyclic alkyl groups, and wherein each R2 is an optionally substituted $C_1$-$C_{20}$ acyl group independently selected from the group consisting of straight chain acyl groups, branched acyl groups, and benzoyl (Bz) groups.

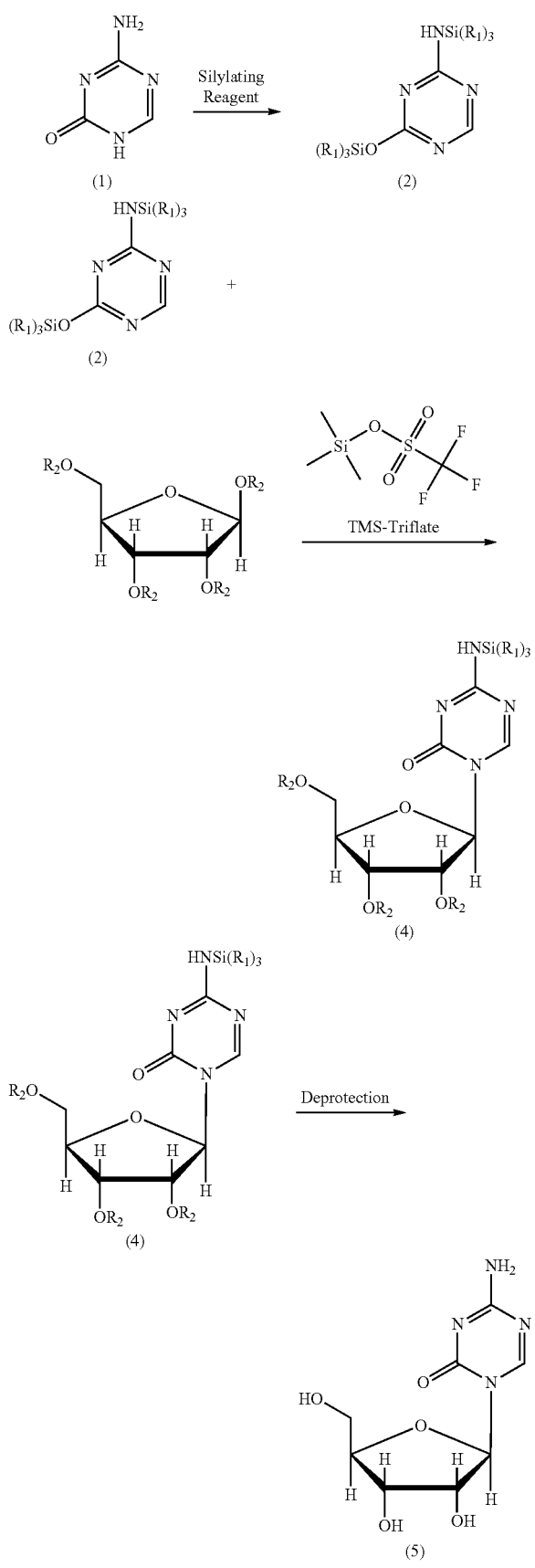

According to this scheme, 5-azacytosine (1) is reacted with a silylating reagent to yield a silylated 5-azacytosine (2). Preferably, the silylating reagent is a trimethylsilyl (TMS) reagent or a mixture of two or more TMS reagents. Preferred TMS reagents include hexamethyldisilizane (HMDS: $(CH_3)_3SiNHSi(CH_3)_3$) and chlorotrimethylsilane (TMSCl: $(CH_3)_3SiCl$). The silylated 5-azacytosine is then reacted with a protected β-D-ribofuranose derivative (3) in the presence of TMS-Triflate (trimethylsilyl trifluoromethanesulfonate). TMS-Triflate catalyzes the coupling reaction, resulting in the formation of a protected 5-azacytidine (4). The protecting groups can be removed by any technique known in the art, including, but not limited to, treatment with methanol/sodium methoxide. The individual reactions of the scheme will now be discussed in detail.

Preparation of Silylated 5-Azacytosine

In one embodiment, the silylated 5-azacytosine is prepared by heating a suspension of 5-azacytosine (1), one or more TMS reagents (present in excess over the 5-azacytosine) and a catalyst, preferably ammonium sulfate, at reflux without a solvent until a clear solution results. Most preferably, the TMS reagent is HMDS, which produces a trimethylsilyl 5-azacytosine derivative ($R_1$=$CH_3$ in the scheme above). By cooling to ambient temperature, the silylated 5-azacytosine crystallizes from the reaction mixture. The silylated 5-azacytosine can then be isolated by any technique known in the art. For example, the silylated 5-azacytosine may be isolated by partially removing excess TMS reagent, followed by addition of a suitable solvent (for example, heptane) and filtration under inert atmosphere. The silylated 5-azacytosine thus isolated is used with or without drying in the coupling step. Alternatively, silylated 5-azacytosine may be isolated by removing TMS reagent by vacuum distillation and then dissolving the residue is in dichloromethane, acetonitrile, or 1,2-dichloroethane for use in the coupling step.

In another embodiment, the silylated 5-azacytosine is prepared "in situ" from 5-azacytosine and an equivalent amount of one or more silylating reagents (preferably a mixture of HMDS and TMSCl) in a suitable solvent in the presence or absence of a catalyst at reflux. Preferably, the solvent is a dry organic solvent, more preferably a dry polar organic solvent, including but not limited to acetonitrile. The resulting silylated 5-azacytosine can be used directly in the coupling step without isolation as described below.

Coupling of Silylated 5-Azacytosine to Sugar

In one embodiment of the invention, coupling of the silylated 5-azacytosine to the sugar is performed by first preparing a cooled mixture (preferably in the range of about 0° C. to about 5° C.) of silylated 5-azacytosine and 1,2,3,5-tetra-O-acetyl-β-D-ribofuranose (or 1-O-acetyl-2,3,5-tri-O-benzoyl-β-D-ribofuranose) in dichloromethane, acetonitrile, or 1,2-dichloroethane. Preferably, the solvent for the coupling step is dichloromethane or 1,2-dichloroethane, most preferably dichloromethane. TMS-triflate is then added to the mixture, preferably at a rate that keeps the temperature below 25° C. After the addition is complete, the clear solution is stirred at ambient temperature for about 2 hours to about 3 hours.

In embodiments which the silylated 5-azacytosine is generated "in situ," the coupling reaction mixture may instead be prepared by adding the sugar and TMS-Triflate directly to the silylation reagents (silylating agent and 5-azacytosine). The sugar and TMS-Triflate can be added concurrently with the silylating reagents, or they may be added at the conclusion of the silylation reaction. Preferably, the TMS-Triflate and the sugar are in the same solvent as used in the silylation reaction, which solvent, as described above, is preferably a dry organic polar solvent including, but not limited to acetonitrile. Using "in situ" generated silylated 5-azacytosine in this manner thus allows one to perform "one pot" silylation and coupling. See Examples 5 and 6.

In embodiments where acetonitrile or other polar solvent is present during the coupling reaction (for example, in embodiments where "one pot" silylation and coupling are performed in a polar solvent), the acetonitrile or other polar solvent is first removed, preferably in vacuum, and the residue is dissolved in dichloromethane or 1,2-dichloroethane prior to quenching. Because polar solvents such are acetonitrile are miscible with water, removing such solvents from the coupling product and then dissolving the product in dry organic non-polar solvents such as dichloromethane or 1,2-dichloromethane minimizes the exposure of the water-sensitive 5-azacytidine to the aqueous phase during extraction/quenching.

Quenching/extraction preferably is performed in a 1/1 w/w NaHCO$_3$/Na$_2$CO$_3$ solution at about 0° C. to about 5° C. Using cooled quenching solution further minimizes the decomposition of the protected 5-azacytidine product during quenching. The organic phase of the quenched reaction is then separated and the water phase extracted with dichloromethane or 1,2-dichloroethane. The combined organic extract is washed with cooled (preferably in the range of about 0° C. to about 5° C.) NaHCO$_3$ solution (preferably 10%) and water, then dried over MgSO$_4$, filtered, and the filtrate concentrated in vacuum. The residue is a protected 5-azacytidine (4). Methanol is then charged to the residue. When dichloromethane is used (either as the coupling solvent or following use of acetonitrile as the coupling solvent), the dichloromethane may be partially removed in vacuum, followed by charging methanol to the mixture, and finally by continued vacuum distillation was continued until substantially all dichloromethane is removed.

As described above, the exposure of protected 5-azacytidine to water can be minimized by using a non-polar dry organic solvent for the coupling step. Alternatively, if a dry organic polar solvent is present at the coupling step, that solvent can be removed and replaced with a dry non-polar organic solvent prior to quenching. The duration of exposure of the protected azacitidine to water (during quenching) also depends on the size of the batch that is processed as small batches can be processed in a shorter time than large batches. Thus, in preferred embodiments of the invention, a single batch of coupling reaction product is split into smaller sub-batches, and each sub-batch is separately subjected to quenching/extraction.

In preferred embodiments, the protecting groups are removed from the protected 5-azacytidine (4) by diluting the methanolic solution of protected 5-azacytidine (4) with methanol, then adding sodium methoxide in methanol (preferably about 25% w/w) to the mixture with stirring at ambient temperature. During this procedure, a white solid separates. The mixture is preferably left stirring for about 8 hours to about 16 hours, following which the solid is filtered off and washed with methanol (until the filtrate is about pH 7). The solid is then dried, preferably in vacuum at about 55° C. to about 65° C. until the weight of the solid remains constant. The solid is crude 5-azacytidine (5).

The crude 5-azacytidine (5) may be purified by any technique known in the art. In preferred embodiments, purification is performed by dissolving the crude product in dimethyl sulfoxide (DMSO) at about 85° C. to about 90° C. under stirring and in an inert atmosphere. Methanol is gradually added to the resulting solution under slow heating, and the mixture is stirred at ambient temperature for about 8 hours to about 16 hours. The resulting recrystallized solid is filtered off, washed with methanol, and then dried, preferably under vacuum at about 85° C. to about 95° C. until the weight remains constant. The overall yield is about 30-40%.

The 5-azacytidine synthesis methods provided by the invention provides a number of clear advantages over the prior art methods. First, the methods allow the manufacturing of pilot plant scale uniform batches of 5-azacytidine. Second, the procedure assures an API without tin or other metallic ion contaminants. Third, there are no difficult to handle phase separation (emulsion) problems in the work-up of the coupling step. Fourth, by removing polar solvents from the coupling reaction prior to quenching/extraction and then dissolving the reaction product is dichloromethane or 1,2-dichloroethane, the exposure of the water-sensitive 5-azacytidine to the aqueous phase is minimized. Finally, the decomposition of the water-sensitive 5-azacytidine is further minimized during the quenching/extraction step by using cooled quenching solutions.

The following examples are provided for illustrative purposes only. They are not to be interpreted as limiting the scope of the invention in any way.

EXAMPLES

Example 1

Preparation of Silylated 5-Azacytosine

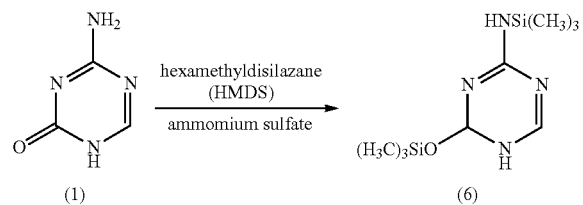

In a 22 L, 3-necked flask, a mixture of 5-azacytosine (1) (2.0 kg, 17.8 mol, 1.07 molar eq.), HMDS (9.162 kg) and ammonium sulfate (40.0 g) was heated at reflux for 2 hours. A fresh amount of ammonium sulfate (20.0 g) was added, and the reflux was continued for 6 hours longer. The initial slurry turned into a clear, pale-yellow, solution and no more gas evolved at the end of the reflux. The excess HMDS was evaporated off in vacuum to obtain an off-white residue, which is trimethylsilylated 5-azacytosine (6).

Example 2

Coupling of Silylated 5-Azacytosine to Sugar

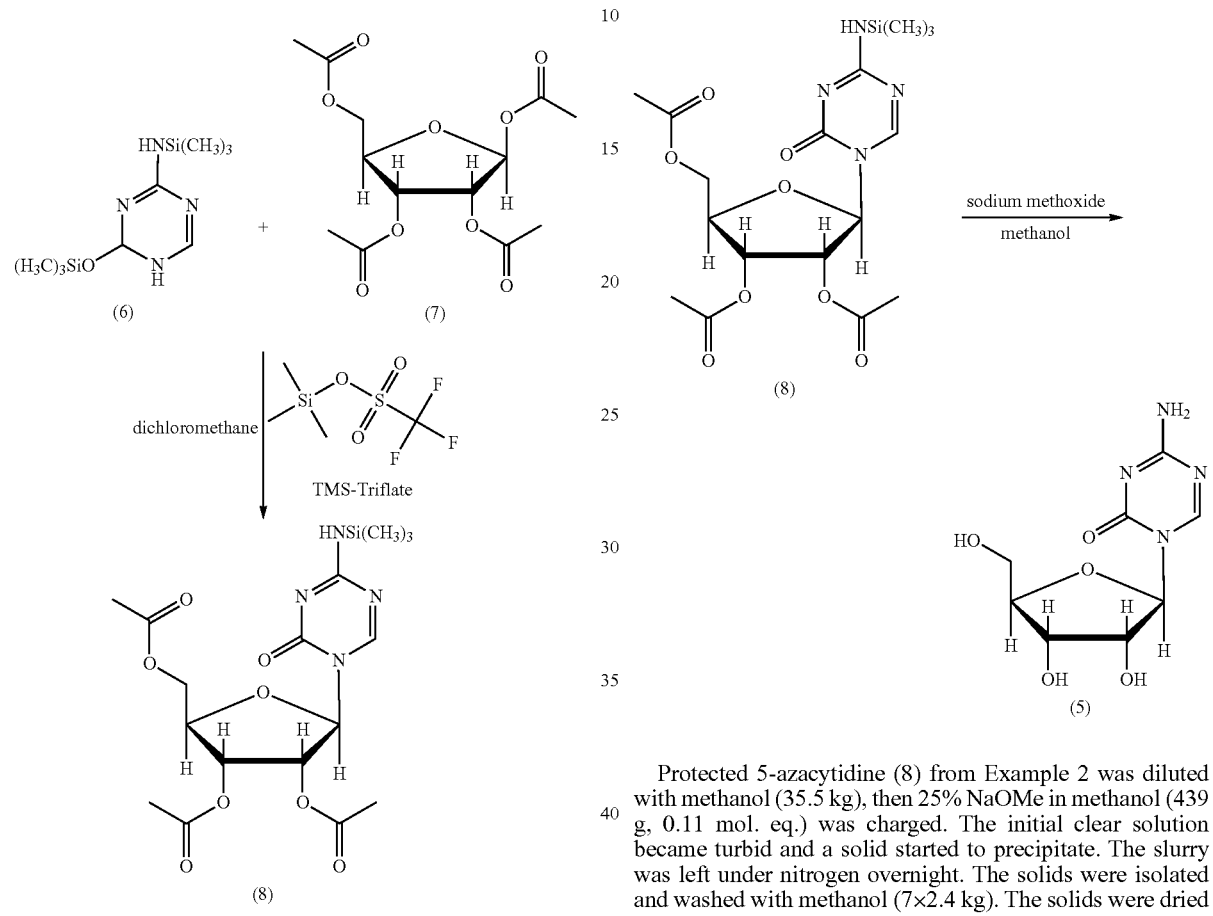

Trimethylsilylated 5-azacytosine (6) prepared according to the method of Example 1 was diluted with anhydrous dichloromethane (18.1 kg) in a 50 L, 3-necked, flask and solid, 1,2,3,5-Tetra-O-acetyl-β-D-ribofuranose (5.330 kg, 16.7 mol) (7) was charged to the mixture. An anhydrous dichloromethane rinse (0.533 kg) was used and the slurry was cooled to 0-5° C. TMS-triflate (4.75 kg, 1.2 molar eq.) was added to the mixture over 5-10 minutes. During the addition, the reaction temperature increased to 15-20° C., and the initial suspension turned into a clear, pale-yellow, solution. After 2 hours of stirring, the solution was poured over a mixture of Na$_2$CO$_3$ (2.00 kg), NaHCO$_3$ (2.00 kg), water (29.9 kg) and ice (20.0 kg). The layers were separated. The water layer was extracted with dichloromethane (8.0 kg). The combined organics were washed with cold (0-5° C.) 10% NaHCO$_3$ (2×10 L). The combined washings were extracted with dichloromethane (8.0 kg). The combined organics were washed with cold water (2×5 kg), dried on MgSO$_4$ (2.0 kg), and filtered. The filtrate and dichloromethane washes on the pad (2×1.32 kg) were combined and reduced in volume using vacuum (~200 mmHg, 30° C.). The distillation was continued until the majority of dichloromethane (app. 85-95% total) was removed. The residue was taken up in methanol (4.0 kg) and the remaining dichloromethane was removed to give a protected 5-azacytidine (8) as an off-white to yellow foam.

Example 3

Deprotection of Protected 5-Azacytidine

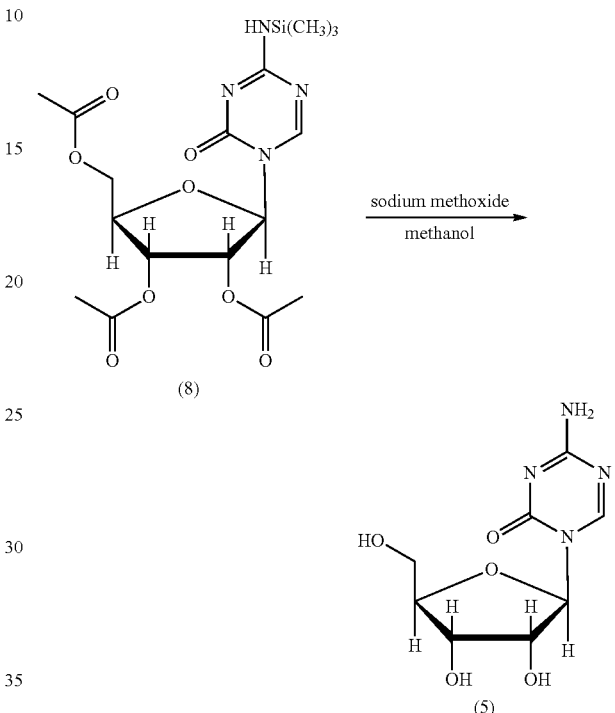

Protected 5-azacytidine (8) from Example 2 was diluted with methanol (35.5 kg), then 25% NaOMe in methanol (439 g, 0.11 mol. eq.) was charged. The initial clear solution became turbid and a solid started to precipitate. The slurry was left under nitrogen overnight. The solids were isolated and washed with methanol (7×2.4 kg). The solids were dried (~28 in Hg and ~85° C.) to a constant weight to give crude 5-azacytidine (1.835 kg; 44.9%) (5).

Example 4

Purification of Crude 5-Azacytidine

Crude 5-azacytidine was purified from DMSO/MeOH as follows: Crude 5-azacytidine (1.829 kg) was dissolved in preheated DMSO (5.016 kg; 87-90° C.) under nitrogen. The solution was diluted with methanol in portions at approximate 10-minute intervals (9×1.4 kg then 1×0.58 kg) while slowly cooling. After the addition, 45-55° C. was maintained for 1 hour and then the mixture was left to cool to ambient temperature overnight. The next day, the solids were isolated at ambient temperature, washed with MeOH (6×0.83 kg), and dried in vacuum (~30 in Hg and ~85° C.) to a constant weight to give 5-azacytidine (1.504 kg; 82.2% recovery).

Example 5

One Pot Synthesis of 5-Azacytidine

A mixture of 5-azacytosine (5.0 g, 44.6 mol), HMDS (6.3 mL, 29.8 mol), and TMSCl (6 mL, 47.3 mmol) in acetonitrile (78 mL) was heated to reflux for 20 hours under an inert atmosphere. TMS-triflate (9 mL, 50 mmol) and 1,2,3,5-tetra-O-acetyl-β-D-ribofuranose (14.2 g, 44.6 mmol were added directly to the silylated 5-azacytosine in acetonitrile. The addition was performed at ambient temperature and under an inert atmosphere. The reaction mixture was maintained under stirring for 20 hours, then poured over a pre-cooled (0-5° C.) sodium bicarbonate solution (10%, 500 mL). The resulting mixture was extracted with dichloromethane (3×75 mL). The combined organic extract was washed with cooled (0-5° C.) 10% sodium bicarbonate (2×25 mL) and brine (2×25 mL), then dried over magnesium sulfate (10.0 g), filtered, and the filtrate concentrated in vacuum to dryness. The off-white foam dissolved in methanol (120 mL) was treated with a solution of 25% sodium methoxide in methanol (1.0 g, 4.62 mmol). Soon a white solid started to separate. The suspension was stirred at ambient temperature for 15 hours, then the solid was filtered off, washed with methanol (3×5 mL) and anhydrous ether (2×5 mL), then dried in vacuum. The crude 5-azacytidine (4.5 g, 41.3%) was further purified from DMSO and methanol (for details see Example 4).

Example 6

One Pot Synthesis of 5-Azacytidine

A mixture of 5-azacytosine, HMDS, and TMSC1 in acetonitrile is heated to reflux for 20 hours under an inert atmosphere. TMS-triflate and 1,2,3,5-tetra-O-acetyl-β-D-ribofuranose are then added directly to the silylated 5-azacytosine in acetonitrile. The addition is performed at ambient temperature and under an inert atmosphere. The reaction mixture is maintained under stirring for 20 hours, then the acetonitrile is removed under vacuum. The solids are then dissolved in dichloromethane, and the mixture is poured over a pre-cooled (0-5° C.) sodium bicarbonate solution (10%). The resulting mixture is extracted with dichloromethane. The combined organic extract is washed with cooled (0-5° C.) 10% sodium bicarbonate and brine, then dried over magnesium sulfate, filtered, and the filtrate concentrated in vacuum to dryness. The off-white foam is dissolved in methanol and treated with a solution of 25% sodium methoxide in methanol. The suspension is stirred at ambient temperature for 15 hours, then the solid is filtered off, washed with methanol and anhydrous ether, then dried in vacuum. The crude 5-azacytidine is further purified from DMSO and methanol (for details see Example 4).

What is claimed is:

1. A method of preparing 5-azacytidine comprising the steps of:
    a) reacting 5-azacytosine with at least one silylating reagent in a dry organic solvent to yield a silylated 5-azacytosine having the structure:

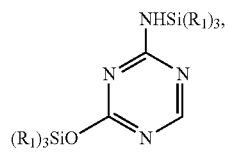

(A)

wherein each $R_1$ is an optionally substituted $C_1$-$C_{20}$ alkyl group independently selected from the group consisting of straight chain alkyl groups, branched alkyl groups, and cyclic alkyl groups;

b) contacting the reaction mixture of Step a) with trimethylsilyl trifluoromethanesulfonate and a compound having the structure;

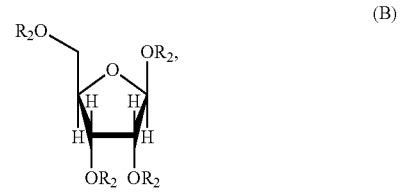

(B)

wherein each $R_2$ is an optionally substituted $C_1$-$C_{20}$ acyl group independently selected from the group consisting of straight chain acyl groups, branched acyl groups, and benzoyl group, to yield a compound having the structure:

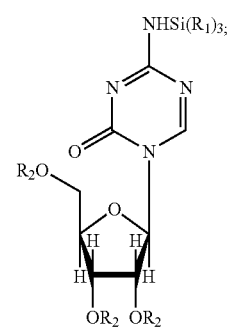

I c) contacting the reaction mixture of Step b) with an aqueous quenching composition and extracting the quenched reaction mixture;
d) removing substantially all of the solvent in the extract of Step c);
e) deprotecting the product in the extract of Step c) with sodium methoxide in methanol to yield 5-azacytidine; and
f) recrystallizing the 5-azacytidine product of Step e) from a solvent system comprising dimethylsulfoxide.

2. The method of claim 1, wherein $R_1$ is methyl.

3. The method of claim 1, wherein each said silylating reagent is a trimethylsilyl (TMS) reagent.

4. The method of claim 3, wherein each said silylating reagent is selected from the group consisting of hexamethyldisilizane and chlorotrimethylsilane.

5. The method of claim 4, wherein the silylating reagent is hexamethyldisilizane.

6. The method of claim 4, wherein the silylating reagents are hexamethyldisilizane and chlorotrimethylsilane.

7. The method of claim 1, wherein the reaction of Step a) is carried out in the presence of ammonium sulfate.

8. The method of claim 1, wherein the dry organic solvent of Step a) is a polar solvent.

9. The method of claim 8, wherein the dry organic solvent of Step a) is acetonitrile.

10. The method of claim 9, wherein the reaction of Step a) is carried out in acetonitrile at refluxing temperature.

11. The method of claim 9, wherein the reaction of Step b) is carried out at ambient temperature.

12. The method of claim 9, wherein the reactions of Step a) and Step b) are carried out under an inert atmosphere.

13. The method of claim 1, wherein Compound (B) is:

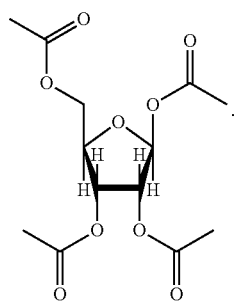

14. The method of claim 1, wherein Compound (B) is:

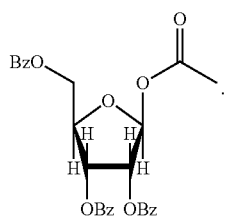

15. The method of claim 9, wherein the method further comprises, between Step b) and Step c), the following steps:
1) removing substantially all of the acetonitrile; and
2) dissolving the product of Step b) in a non-polar organic solvent.

16. The method of claim 15, wherein the non-polar organic solvent is dichloromethane or 1,2-dichloroethane.

17. The method of claim 15, wherein the non-polar organic solvent is dichloromethane.

18. The method of claim 1, wherein the aqueous quenching composition of Step c) comprises an aqueous solution of sodium bicarbonate.

19. The method of claim 1, wherein the aqueous quenching composition of Step c) comprises an aqueous solution of sodium carbonate and sodium bicarbonate.

20. The method of claim 19, wherein the sodium carbonate and sodium bicarbonate have a weight ratio of about 1:1.

21. The method of claim 1, wherein the aqueous quenching composition of Step c) is at a temperature of between about 0° C. and about 5° C.

22. The method of claim 1, wherein the quenched reaction mixture in Step c) is extracted with dichloromethane.

23. The method of claim 22, wherein the dichloromethane extract is washed with a cooled solution comprising sodium bicarbonate.

24. The method of claim 23, wherein the dichloromethane extract is further washed with brine, dried over $MgSO_4$, and filtered.

25. The method of claim 1, wherein the reaction of Step e) is carried out at ambient temperature.

26. The method of claim 1, wherein the 5-azacytidine product of Step e) forms a solid and separates from the reaction mixture.

27. The method of claim 1, wherein the 5-azacytidine product of Step e) is isolated by filtration.

28. The method of claim 1, wherein Step f) comprises:
i) dissolving the 5-azacytidine product of Step e) in dimethylsulfoxide;
ii) adding methanol to the solution of i); and
iii) isolating the recrystallized product.

29. The method of claim 1, wherein Step f) comprises:
i) dissolving the 5-azacytidine product of Step e) in hot dimethylsulfoxide;
ii) adding methanol to the solution of i) and cooling the mixture; and
iii) isolating the recrystallized product.

30. The method of claim 29, wherein the 5-azacytidine product of Step e) is dissolved in dimethylsulfoxide heated to a temperature of from about 85° C. to about 90° C.

31. The method of claim 29, wherein the mixture of Step ii) is cooled to ambient temperature.

* * * * *